US009138149B2

(12) United States Patent
Kinsley et al.

(10) Patent No.: US 9,138,149 B2
(45) Date of Patent: Sep. 22, 2015

(54) SYSTEMS AND METHODS FOR DETERMINING PATIENT TEMPERATURE

(75) Inventors: Matthew J. Kinsley, Marcellus, NY (US); David E. Quinn, Auburn, NY (US); John A. Lane, Weedsport, NY (US); Michael J. Anson, Syracuse, NY (US); Henry J. Smith, III, Auburn, NY (US); Matthew D. Mullin, Memphis, NY (US); Eric Lawson, Auburn, NY (US)

(73) Assignee: WELCH ALLYN, INC., Skaneateles Falls, NY (US)

( * ) Notice: Subject to any disclaimer, the term of this patent is extended or adjusted under 35 U.S.C. 154(b) by 232 days.

(21) Appl. No.: 13/423,785

(22) Filed: Mar. 19, 2012

(65) Prior Publication Data
US 2013/0245457 A1   Sep. 19, 2013

(51) Int. Cl.
*A61B 6/00* (2006.01)
*A61B 5/01* (2006.01)
*A61B 5/00* (2006.01)
*G01J 5/02* (2006.01)
*G01J 5/04* (2006.01)
*G01J 5/18* (2006.01)
*G01J 5/08* (2006.01)
*G01J 5/00* (2006.01)

(52) U.S. Cl.
CPC .............. *A61B 5/01* (2013.01); *A61B 5/6886* (2013.01); *G01J 5/0025* (2013.01); *G01J 5/021* (2013.01); *G01J 5/025* (2013.01); *G01J 5/0265* (2013.01); *G01J 5/041* (2013.01); *G01J 5/0806* (2013.01); *G01J 5/0846* (2013.01); *G01J 5/18* (2013.01); *A61B 2562/247* (2013.01)

(58) Field of Classification Search
USPC .............. 600/427, 438–439, 473; 601/3; 607/100–104
See application file for complete search history.

(56) References Cited

U.S. PATENT DOCUMENTS

| | | | |
|---|---|---|---|
| 3,373,611 A | 3/1968 | Trott | |
| 4,343,185 A * | 8/1982 | Knute | 374/158 |
| 4,737,038 A | 4/1988 | Dostoomian | |
| 4,784,149 A | 11/1988 | Berman et al. | |
| 6,109,784 A | 8/2000 | Weiss | |
| 6,386,757 B1 | 5/2002 | Konno | |

(Continued)

FOREIGN PATENT DOCUMENTS

| | | |
|---|---|---|
| EP | 721101 A3 | 2/1997 |
| EP | 1757862 A2 | 2/2007 |

(Continued)

OTHER PUBLICATIONS

International Search Report and Written Opinion mailed Jul. 15, 2013, PCT/US2013/032286, 11 pages.

(Continued)

*Primary Examiner* — Joel F Brutus

(57) ABSTRACT

A temperature probe includes a handle and a shaft extending from the handle. The shaft includes a distal end, a proximal end, and a tip at the distal end. The temperature probe also includes a capacitance sensor disposed on one of the handle and the shaft, the capacitance sensor configured to measure a change in capacitance when positioned proximate a conductor. The temperature probe further includes a temperature sensor disposed on the shaft, the temperature sensor configured to measure a body cavity temperature of a patient.

20 Claims, 5 Drawing Sheets

(56) References Cited

U.S. PATENT DOCUMENTS

| | | |
|---|---|---|
| 6,647,284 B1 | 11/2003 | Lee |
| 6,758,835 B2 * | 7/2004 | Close et al. ............ 604/272 |
| 6,789,936 B1 | 9/2004 | Kraus et al. |
| 7,484,884 B2 | 2/2009 | Lane et al. |
| 7,686,506 B2 | 3/2010 | Babkes et al. |
| 8,187,270 B2 | 5/2012 | Auth et al. |
| 2004/0170216 A1 | 9/2004 | Russak et al. |
| 2005/0094705 A1 | 5/2005 | Chi |
| 2006/0293600 A1 * | 12/2006 | Wawro et al. ............ 600/490 |
| 2007/0047618 A1 | 3/2007 | Howanski |
| 2007/0055171 A1 | 3/2007 | Fraden |
| 2007/0242726 A1 | 10/2007 | Medero |
| 2008/0080593 A1 * | 4/2008 | Lane et al. ............ 374/208 |
| 2008/0107152 A1 | 5/2008 | Ishimaru et al. |
| 2009/0275838 A1 * | 11/2009 | Marshall et al. ............ 600/463 |
| 2010/0113894 A1 * | 5/2010 | Padiy ............ 600/301 |
| 2010/0265986 A1 | 10/2010 | Mullin et al. |
| 2011/0106484 A1 | 5/2011 | Quinn et al. |
| 2011/0118623 A1 * | 5/2011 | Nakanishi et al. ............ 600/549 |
| 2011/0130890 A1 | 6/2011 | Tojo et al. |
| 2011/0190767 A1 | 8/2011 | Kwan et al. |
| 2011/0216806 A1 | 9/2011 | Weng |
| 2011/0224668 A1 * | 9/2011 | Johnson et al. ............ 606/42 |
| 2013/0023772 A1 | 1/2013 | Kinsley et al. |

FOREIGN PATENT DOCUMENTS

| | | |
|---|---|---|
| JP | 2000005137 A | 1/2000 |
| JP | 2000041955 A | 2/2000 |
| JP | 2006-308312 A | 11/2006 |
| WO | 03002966 A1 | 1/2003 |
| WO | 2011113727 A1 | 9/2011 |

OTHER PUBLICATIONS

Conductive Material Thickness Measurement with Capacitive Sensors, http://www.lionprecision.com/tech-library/appnotes/cap-0030-thickness-measurement.html accessed: Mar. 22, 2012.

International Search Report and Written Opinion for PCT/US2014/014484, Dated May 16, 2014 (12 pages).

Anal Probe with Adjustable Depth by ArtraMaples88 on Oct. 18, 2011 from gerd.goohealthlife.com, http://www.zimbio.com/Hemroids/articles/grbTA4WZUgx/Anal+Probe+Adjustable+Depth accessed: Jan. 25, 2012.

Vicks Baby Rectal Thermometer, http://www.amazon.com/Vicks-V934-Baby-Rectal-Thermometer/db/B0002AHVZU, accessed: Jan. 25, 2012.

Ultrasound Rectal Probe R7.5, http://www.alibaba.com/product-gs/490643023/utrasound_rectal_probe_R7_5.html, accessed: Jan. 25, 2012.

\* cited by examiner

SYSTEMS AND METHODS FOR DETERMINING PATIENT TEMPERATURE

FIELD OF THE INVENTION

The present disclosure relates to systems and methods for temperature determination and, in particular, to systems and methods for determining a patient temperature.

BACKGROUND OF THE INVENTION

Measuring patient temperature is a common first step in diagnosing illnesses. Physicians commonly use a variety of methods for determining patient temperature, including, for example, obtaining temperature measurements with a thermometer. While thermometers utilizing mercury have been in existence for many years, modern thermometers typically employ one or more electronic sensors configured to measure patient temperature. Such sensors may take one or more measurements over a relatively short period of time. Based on these measurements, the thermometer may generate a predicted internal and/or core temperature of the patient. In generating this predicted temperature, it is common practice to insert at least a portion of the thermometer into a cover prior to taking temperature measurements. Known thermometers may then sense the ambient temperature of a body cavity of the patient, and may use this sensed ambient temperature in determining a patient's core temperature.

However, determining a patient's core temperature as described above can produce inaccurate results. For example, due to inherent variations in the manufacturing process, the covers utilized with such thermometers often have thicknesses that vary within a certain tolerance range. Although the variations in probe cover thickness can be a source of significant error in the core temperature determination, it can be difficult and expensive to manufacture probe covers within a relatively narrow thickness tolerance range. Thus, in an effort to minimize the effect of such error, modern thermometers may utilize algorithms that make predetermined estimates to compensate for these thickness variations. Compensating for such variations in this way may, however, introduce additional error into the core temperature determination, thereby further reducing the accuracy of such determinations.

The exemplary embodiments of the present disclosure are directed toward overcoming the deficiencies described above.

SUMMARY

In an exemplary embodiment of the present disclosure, a temperature probe includes a handle and a shaft extending from the handle. The shaft includes a distal end, a proximal end, and a tip at the distal end. The temperature probe also includes a capacitance sensor disposed on one of the handle and the shaft, the capacitance sensor configured to measure a change in capacitance when positioned proximate a conductor. The temperature probe further includes a temperature sensor disposed on the shaft, the temperature sensor configured to measure a body cavity temperature of a patient.

In another exemplary embodiment of the present disclosure, a method of determining a core temperature of a patient includes determining a first capacitance with a capacitance sensor of a temperature probe, determining a difference between the first capacitance and a known capacitance stored in a memory associated with the temperature probe, and inserting a portion of the temperature probe into a body cavity of the patient. The method also includes measuring a body cavity temperature of the patient with the temperature probe, and calculating the core temperature of the patient based on the difference and the body cavity temperature.

In a further exemplary embodiment of the present disclosure, a temperature measurement system includes a storage container having a front, a back, at least two sides, a top, and a bottom wall disposed opposite the top. The front, back, and at least two sides are disposed orthogonal to the bottom wall, and the top includes an opening. The system also includes a conductor disposed on the bottom wall, and a plurality of probe covers disposed within the storage container and accessible for removal through the opening. A distal end of each probe cover of the plurality of probe covers contacting the conductor on the bottom wall prior to removal from the storage container.

DETAILED DESCRIPTION

Figure 1:
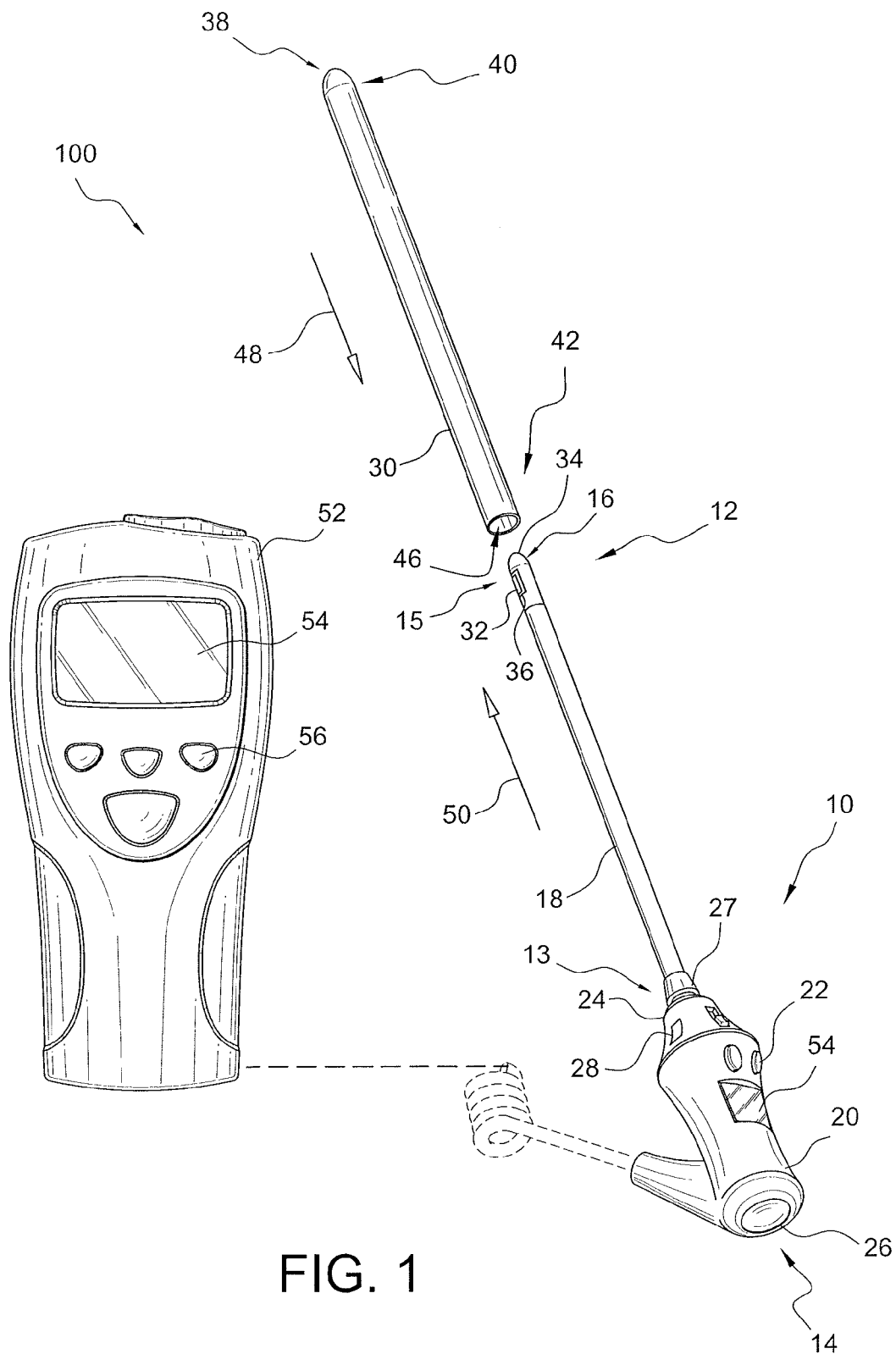
FIG. 1 illustrates a temperature probe of an exemplary temperature measurement system.

FIG. 1 illustrates an exemplary temperature probe 10 of the present disclosure. It is understood that the implementation of the disclosed technology in a temperature probe is merely exemplary. The disclosed technology may be applicable to any other probes, speculums, endoscopes, and/or other medical devices using a sheath and/or cover to protect the device from contaminants present on a surface and/or within a body cavity, where the characteristics of the sheath/cover affect the accuracy of the gathered data. The temperature probe 10 may include, for example, a shaft 18 extending from a handle 20. A distal end 15 of the shaft 18 may define a distal end 12 of the temperature probe 10, and the handle 20 may define a proximal end 14 of the probe 10. The shaft 18 may also define a tip 16 disposed at the distal end 15. The tip 16 may be sufficiently rounded, atraumatic, and/or otherwise configured so as not to cause injury to a patient upon contact with a body surface and/or at least partial insertion of the shaft 18 within one or more body cavities of the patient. As used herein, the term "patient" may include any human acting to measure his/her own temperature (such as by using a temperature probe 10 without interaction from a healthcare professional), or any human or animal whose temperature is being measured. In an exemplary embodiment in which the temperature probe 10 is utilized to sense, measure, calculate, and/or otherwise determine a temperature of the patient, it is understood that such body cavities may include the mouth, rectum, underarm, and/or other known body cavities from which a temperature may be sensed. The shaft 18 and/or the handle 20 may be made from any material and/or combinations of materials commonly used in medical and/or examination procedures. Such materials may include, for example, plastics, polymers, composites, stainless steel, and/or any other like materials. Such materials may be suitable for repeated use and/or repeated sanitation. Accordingly, in an exemplary embodiment of the present disclosure, the temperature probe 10 and/or its components may be substantially waterproof. One or more waterproof seals may be included and/or otherwise utilized with components of the temperature probe 10 to facilitate such repeated sanitation and/or use.

The handle 20 may include one or more operator interfaces 22. Such operator interfaces 22 may be configured to assist in performing one or more functions of the temperature probe 10. For example, the operator interfaces 22 may comprise any combination of switches, buttons, levers, knobs, dials, keys, and/or other like components configured to activate, deactivate, manipulate, and/or otherwise control components of the temperature probe 10. Such operator interfaces 22 may, for example, assist the user in toggling through and/or selecting one or more modes of operation of the temperature probe 10, enabling and/or disabling one or more alarms or signals associated with operation of the probe 10, initiating a single substantially instantaneous temperature determination, initiating a substantially continuous and/or repeating temperature determination, and/or other like modes, functions, or operations.

In an exemplary embodiment, at least one of the operator interfaces 22 may comprise an ejector mechanism 26 disposed at the proximal end 14 of the temperature probe 10. As will be described in greater detail below, at least a portion of the temperature probe 10 may be inserted into a probe cover 30 before and/or during use, and such an ejector mechanism 26 may be configured to assist in removing the probe cover 30 from the temperature probe 10. In an exemplary embodiment, actuating the ejector mechanism 26 may extend the shaft 18, in the direction of arrow 50, a desired distance from a base 24 formed at a proximal end 13 of the shaft 18. Extending the shaft 18 in this way may eject and/or otherwise remove a probe cover 30 from the shaft 18. In particular, extending the shaft 18 in the direction of arrow 50 may overcome a retention force provided by one or more shoulders, rings, tabs, extensions, and/or other like stationary retention components 27 of the temperature probe 10. Such stationary retention components 27 may be disposed, for example, proximate the base 24.

In further exemplary embodiment, the ejector mechanism 26 may be operably connected to one or more moveable components disposed at or on the base 24. In such exemplary embodiments, actuating the ejector mechanism 26 may move one or more such components in the direction of arrow 50 to assist in removing the probe cover 30 from the shaft 18. For example, such moveable components may comprise one or more fingers, hooks, shoulders, arms, tabs, rings, and/or other like moveable components configured to assist in ejecting the probe cover 30 from the base 24 of the shaft 18 after use. Such components may be movable with respect to, for example, the base 24 and/or the shaft 18, and such components may be movable in, for example, a direction substantially parallel to the shaft 18. In additional exemplary embodiments, such components may be movable in an arcuate path relative to the shaft 18. Movement of such components may assist in bending, flexing, and/or otherwise deforming at least a portion of the probe cover 30. For example, such components may be movable along one or more surfaces of the probe cover 30, and such movement may assist in flexing at least a portion of the probe cover 30. Such flexing may ultimately overcome a retention force provided by one or more of the retention components 27 described above, thereby releasing the probe cover 30 from the temperature probe 10.

In additional exemplary embodiments, one or more operator interfaces 22 may be configured to assist in controlling one or more corresponding sensors associated with the temperature probe 10. For example, the operator interfaces 22 may be operably connected to first and second sensors 32, 34 disposed on the handle 20 and/or the shaft 18. In exemplary embodiments, the first and second sensors 32, 34 may be embedded within and/or otherwise formed integrally with the shaft 18. In such exemplary embodiments, the sensors 32, 34 may be positioned just beneath an outer surface of the shaft 18 such that the shaft 18 may retain a substantially smooth, substantially cylindrical shape. In such exemplary embodiments, it is understood that the sensors 32, 34 may be electrically, operably, and/or otherwise connected to the operator interfaces 22 and/or other components of the temperature probe 10 via wireless or electrical connections embedded within and/or running along a length of the shaft 18 beneath the outer surface of the shaft 18.

In an exemplary embodiment, one or more of the sensors 32, 34 may comprise any type of temperature sensor known in the art. For example, the sensors 32, 34 may be the same type of sensor. Alternatively, the sensors 32, 34 may comprise different types of sensors configured to sense one or more different characteristics of a patient. In an exemplary embodiment, at least one of the first and second sensors 32, 34 may comprise a thermocouple and/or a thermistor configured to sense a temperature associated with such a patient. For example, such a sensor may be configured to measure a temperature of the body cavity into which the temperature probe 10 has been inserted. For example, in embodiments in which the shaft 18 of the temperature probe 10 is inserted into the mouth of the patient, such a sensor may be utilized to measure a temperature of a mouth surface.

At least one of the sensors 32, 34 may also comprise an infrared temperature sensor, such as, for example, a thermopile and/or other like infrared-based temperature-sensing components. Such a sensor may be configured to convert thermal energy into electrical energy, and may comprise two or more thermocouples connected in series or in parallel. Such components may be configured to generate an output voltage proportional to a local temperature difference and/or temperature gradient. In an exemplary embodiment in which the one or more of the sensors 32, 34 comprise a thermopile, the temperature probe 10 may comprise, for example, an infrared temperature probe and/or other like infrared thermometer.

In such embodiments, an exemplary infrared temperature probe 10 may utilize at least a portion of the thermal radiation emitted by the patient and/or the body cavity of the patient into which the temperature probe 10 has been inserted in order to estimate, infer, calculate, and/or otherwise determine a core temperature of a patient temperature. Such an exemplary temperature probe 10 may utilize signals received by at least one of the first and second sensors 32, 34 to determine an amount of infrared radiation emitted by the patient. Using a known transmissivity and/or other characteristic of the patient, such infrared temperature probes 10 may be capable of determining a temperature of the patient, including a body cavity temperature of the patient and/or a core temperature of the patient.

In a further exemplary embodiment, at least one of the sensors 32, 34 may comprise a capacitance sensor configured to measure a capacitance and/or a change in capacitance. For example, in an embodiment in which the first sensor 32 comprises a temperature sensor, the second sensor 34 may comprise a capacitance sensor configured to measure a change in capacitance when positioned proximate a conductor. Such a capacitance sensor 34 may comprise any type of sensor configured to detect a conductive substance or other substance having a dielectric constant different than that of air. For example, such a capacitance sensor may include a first conductive layer made from copper, indium tin oxide, silver, carbon, printed ink, and/or any other known conductive material. During use, a voltage may be applied to the conductive layer, resulting in the formation of an electric field extending from the conductive layer. When a conductor is disposed within the electric field, a capacitor is formed, and the capacitance sensor 34 may measure a change in capacitance resulting from the conductor's presence within the electric field. For example, the capacitance may change as the distance between the conductive layer of the capacitance sensor 34 and the conductor changes. The capacitance sensor 34 may be configured to generate one or more signals indicative of such a capacitance and/or a change in capacitance, and the change in capacitance may be based on the distance between the capacitance sensor 34 and the conductor.

A variety of converters and/or other known electrical components may be used with the capacitance sensors 34 of the present disclosure to condition and/or interpret the signal generated by the capacitance sensor 34. For example, the sensors 32, 34 may be operably, controllably, electrically, and/or otherwise connected to a controller 52, and such a converter may be a software and/or hardware component of the controller 52. In such an exemplary embodiment, the controller 52 may be configured to assist in calculating and/or otherwise determining a core temperature of a patient based on the temperature measurements, capacitance measurements, and/or other measurements made by the first and second sensors 32, 34. In exemplary embodiments, such converters may convert the capacitive input signals generated by the capacitance sensor 34 into digital values or "counts" representative of the measured capacitance.

Figure 2:
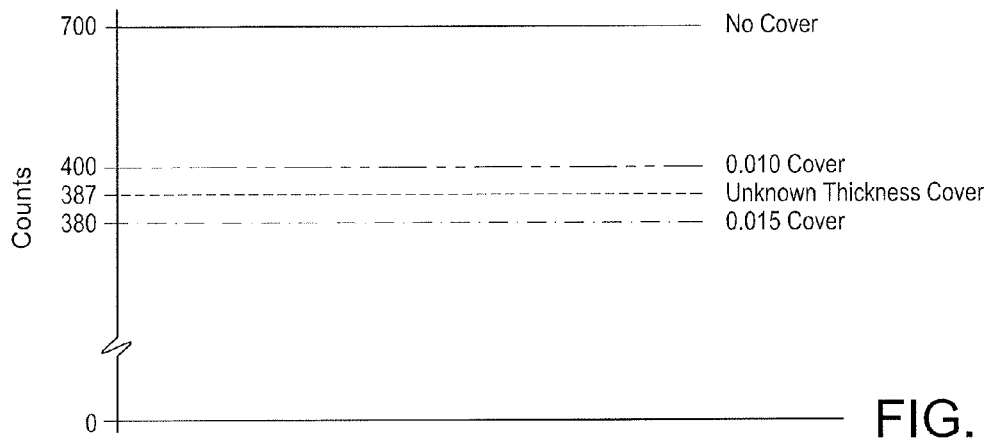
FIG. 2 illustrates a capacitance plot according to an exemplary embodiment of the present disclosure.
Figure 5:
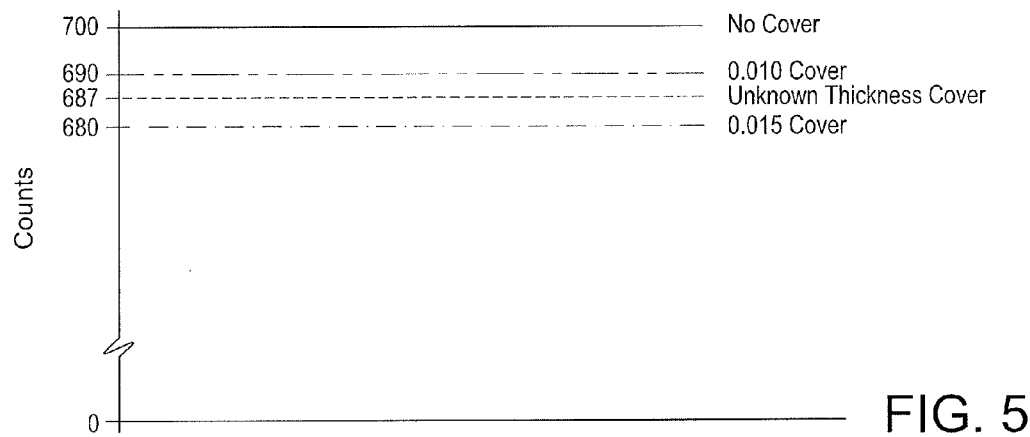
FIG. 5 illustrates a capacitance plot according to another exemplary embodiment of the present disclosure.
Figure 8:
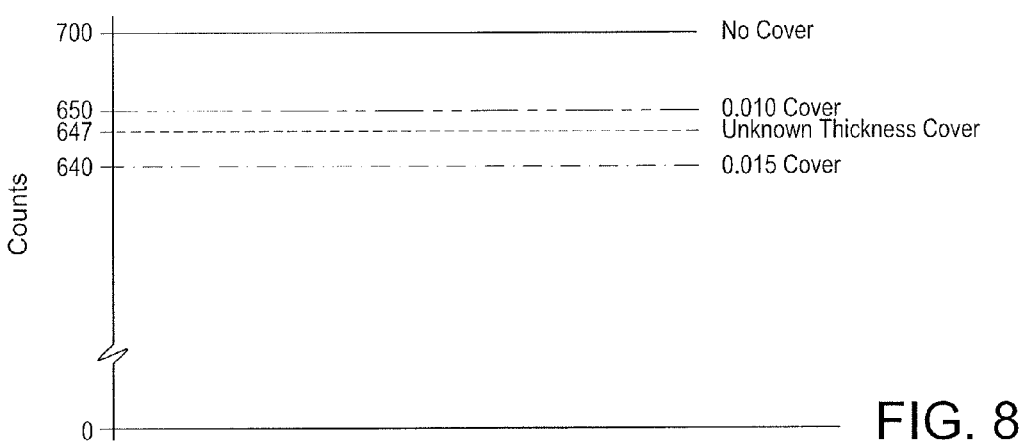
FIG. 8 illustrates a capacitance plot according to a further exemplary embodiment of the present disclosure.

As will be described in greater detail below, FIGS. 2, 5, and 8 illustrate various capacitance count plots of the present disclosure in which exemplary count values are shown for purposes of discussion. As exemplified by FIGS. 2, 5, and 8, count value (i.e., measured capacitance) changes are based on the proximity of the capacitance sensor 34 to the conductor. For example, the measured capacitance may have its highest value (for example, 700 counts) when the capacitance sensor 34 is placed in direct contact with the conductor and no probe cover 30 is disposed on the shaft 18. Such a capacitance value may be stored within a memory of the controller 52 and may be utilized as a known reference value for determining, for example, the thickness of one or more probe covers 30 disposed on the shaft 18. The measured capacitance may decrease as the conductor is spaced and/or separated from the capacitance sensor 34, such as by a probe cover 30. As shown in FIGS. 2, 5, and 8, the measured capacitance may vary based on the thickness of the probe cover 30 being used, and the use of a thicker probe cover 30 may result in a lower capacitance value than the use of a relatively thinner probe cover 30. Thus, such measured and known capacitance values may be used by the controller 52 to determine an unknown thickness of a probe cover 30 being used.

Figure 7:
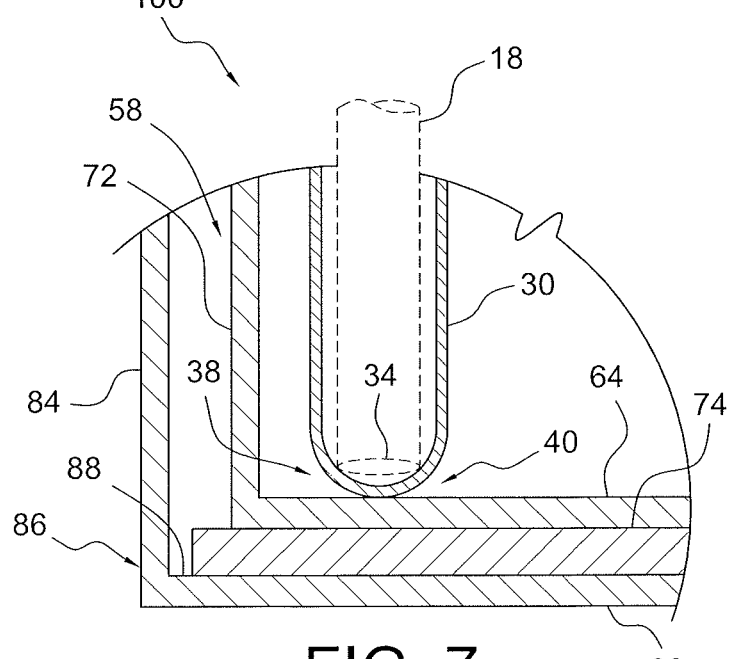
FIG. 7 illustrates a cutaway view of a portion of the user station shown in FIG. 6.

The conductors described above may comprise any conductive material and/or structure known in the art. In some embodiments, the body cavity of the patient from which a body cavity temperature is measured may be a conductor affecting the capacitance measured by the sensor 34. For example, in embodiments in which a body cavity temperature is measured by inserting the shaft 18 into the patient's mouth, the conductor may comprise the patient's tongue and/or other parts of the patient's mouth. As shown in FIGS. 4 and 7, in further exemplary embodiments, a conductor 74 may comprise a metallic sheet, film, plate, layer, coating, and/or other like structure. As will be described in greater detail below with respect to FIGS. 3 and 4, such a conductor 74 may be disposed within a storage container 58 housing one or more probe covers 30.

Figure 6:
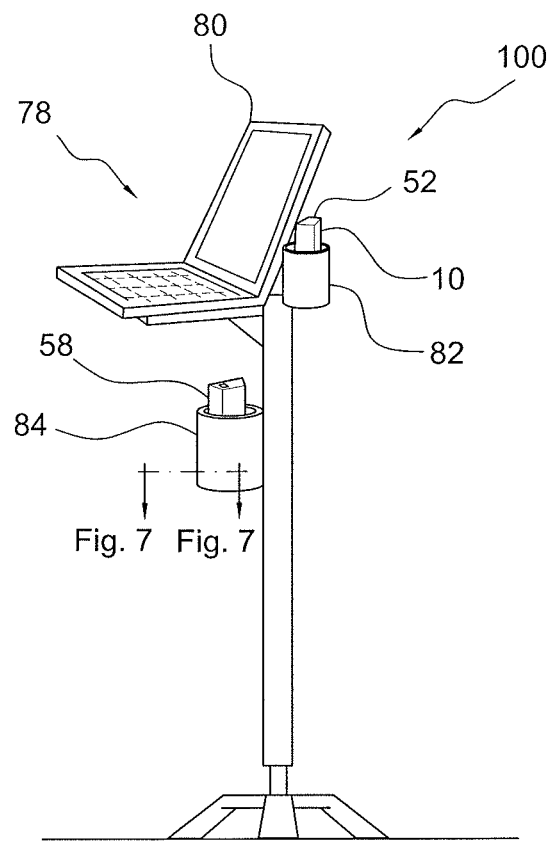
FIG. 6 illustrates a user station of an exemplary temperature measurement system.

Alternatively, in exemplary embodiments in which the storage container 58 is disposed within a receptacle 84 of a user station 78 (FIG. 6), such a conductor 74 may be disposed on a base 86 (FIG. 7) of the receptacle 84, and external to the storage container 58. Such a user station 78 may include one or more operator interfaces 80 configured for communication with the temperature probe 10 and/or the controller 52. Such a user station 78 may also include one or more additional receptacles 82 for storing the temperature probe 10 and/or the controller 52.

FIG. 7 illustrates a cutaway view of a portion of an exemplary receptacle 84 having a storage container 58 disposed therein. The receptacle 84 may include one or more walls extending orthogonal from the base 86, and the base 86 may include an inner surface 88 and an outer surface 90. Although FIG. 7 illustrates the conductor 74 being disposed on the inner surface 88, in further exemplary embodiments, the conductor 74 may be disposed on the outer surface 90 and/or on one or more of the walls extending from the base 86. In still further exemplary embodiments, the conductor 74 may be formed integrally with the base 86, and in such exemplary embodiments, the base 86 may be formed from one or more metallic and/or other conductive materials to provide the functionality of the conductors 74 described herein. Likewise, although FIG. 4 illustrates the conductor 74 being disposed on a bottom wall 64 of the storage container 58, in additional exemplary embodiments, the conductor 74 may be formed integrally with the bottom wall 64 and/or other components of the storage container 58. In such exemplary embodiments, the bottom wall 64 and/or other components of the storage container 58 may be formed from one or more metallic and/or other conductive materials to provide the functionality of the conductors 74 described herein.

Figure 9:
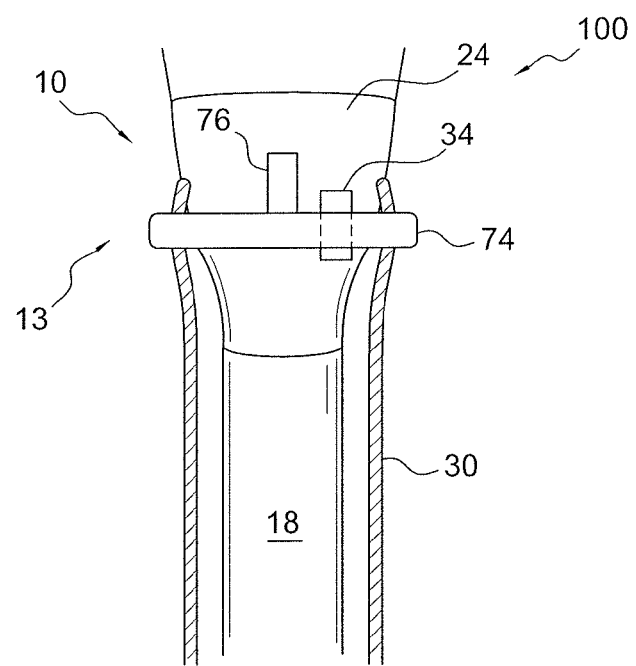
FIG. 9 illustrates a partial view of a temperature probe according to another exemplary embodiment of the present disclosure.

In still further exemplary embodiments, the conductor 74 may comprise a metallic and/or otherwise conductive ring disposed proximate the capacitance sensor 34. For example, as shown in FIG. 9, the capacitance sensor 34 may be disposed proximate the proximal end 13 of the shaft 18, and the ring-shaped conductor 74 may encircle at least a portion of the proximal end 13. In such exemplary embodiments, the conductor 74 may be connected to the temperature probe 10 in any known way, and the conductor 74 may be spaced from the outer surface of the shaft 18 such that a probe cover 30 may be disposed on the shaft 18 and/or removably connected to the shaft 18 without interference from the conductor 74. For example, such an exemplary ring-shaped conductor 74 may be connected to the handle 20 and/or the shaft 18 by one or more conductive or non-conductive mounts 76 extending from the temperature probe 10. The mount 76 may assist in spacing the conductor 74 from the outer surface of the shaft 18 such that the probe cover 30 may be disposed on the shaft 18 between the conductor 74 and a portion of the capacitance sensor 34. In such exemplary embodiments, the conductor 74 may overlay the portion of the capacitance sensor 34, and may be disposed within an electric field generated by the capacitance sensor 34 during use. Thus, disposing the probe cover 30 between the capacitance sensor 34 and the ring-shaped conductor 74 may change the capacitance value measured by the capacitance sensor 34. For example, disposing a thicker probe cover 30 on the shaft 18 between the capacitance sensor 34 and the ring-shaped conductor 74 may result in a lower measured capacitance value than the use of a relatively thinner probe cover 30.

Thus, as described above, the signal generated by the capacitance sensor 34 may be indicative of the thickness of the probe cover 30 disposed on the shaft 18 and, in particular, may be indicative of the change in capacitance sensed by the capacitance sensor 34. This change in capacitance may be based on the distance between the capacitance sensor 34 and the conductor 74. As shown in FIG. 4, this change in capacitance may result from the capacitance sensor 34 being spaced from the conductor 74 by a probe cover 30 in contact with both the distal end 15 of the shaft 15 and the conductor 74. As shown in FIG. 7, such a change in capacitance may also result from the capacitance sensor 34 being spaced from the conductor 74 by both a probe cover 30 and the bottom wall 64 of the storage container 58. Moreover, as shown in FIG. 9, such a change in capacitance may also result from the probe cover 30 being disposed between the conductor 74 and the capacitance sensor 34. Because the probe cover 30 may have a different dielectric constant than air, the probe cover 30 may attenuate the corresponding measured capacitance value.

With continued reference to FIG. 1, at least one of the sensors 32, 34 may additionally include at least one window, lens, and/or other like optical component 36 positioned proximate thereto. For example, such an optical component 36 may be disposed substantially flush and/or coplanar with the outer surface of the shaft 18. In an exemplary embodiment in which the shaft 18 is substantially cylindrical, such an optical component 36 may be substantially curved so as to match the radius of curvature of the shaft 18. Such optical components 36 may assist in, for example, focusing and/or transmitting infrared radiation between the thermopile and the body cavity of the patient. Such optical components 36 may also assist in protecting the thermopile, thermocouple, thermistor, and/or other sensor components during use of the temperature probe 10, and may assist in forming a substantially fluid tight compartment within the shaft 18 so as to protect sensor components from contact with bodily fluids, cleaning solutions, and/or other liquids. It is understood that such optical components 36 may be substantially transparent to assist in the transmission of infrared radiation. Such optical components 36 may also be highly electrically transmissive and may have a negligible effect on, for example, an electric field generated by one or more of the sensors 32, 34.

The handle 20 may also include one or more displays 54 operably connected to the controller 52. The display 54 may comprise, for example, a liquid crystal display (LCD) screen, a light emitting diode (LED) display, a digital read-out, and/or any other like components configured to communicate information to the user of the temperature probe 10. Such displays 54 may be configured to indicate, for example, one or more temperatures measured by the sensors 32, 34; one or more capacitance values and/or changes in capacitance measured by the sensors 32, 34; one or more temperatures determined based on signals received from the one or more sensors 32, 34; and/or any other information that may be useful during operation of the temperature probe 10. The display 54 may be configured to communicate such information substantially instantaneously and/or substantially continuously, depending on the mode of operation of the temperature probe 10. Such a display 54 may also indicate whether or not the temperature probe 10 is turned on and whether a probe cover 30 has been connected to the temperature probe 10. The display 54 may also be configured to indicate the mode of operation of the temperature probe 10 (for example, continuous or instantaneous modes of temperature calculation), as well as whether one or more threshold temperatures, threshold temperature change rates, and/or other sensed metric thresholds have been met or exceeded. The display 54 may be, for example, a substantially numerical digital display, and may also be configured to display any other typical operating information, such as, for example, a temperature versus time trend line or other graphical depictions. Such graphical depictions may also include one or more capacitance plots of the type illustrated in FIGS. 2, 5, and 8.

The temperature probe 10 may also include one or more signal devices (not shown) operably connected to the controller 52. Such signal devices may include, for example, one or more lights, LEDs, speakers, and/or other like devices configured to emit an audible and/or optical alarm or signal in response to a command or signal from the controller 52. Such an alarm or other signal may be initiated by, for example, the controller 52 when the calculated temperature meets or exceeds a threshold temperature. In additional exemplary embodiments, such an alarm or signal may be initiated during a substantially continuous temperature calculation operation where the rate of patient temperature change meets or exceeds a predetermined temperature change rate threshold. In additional exemplary embodiments, such signal/devices may be disposed on and/or otherwise associated with the controller 52.

The controller 52 may be operably connected to the operator interfaces 22, display 54, sensors 32, 34, and/or other components of the temperature probe 10, and the controller 52 may be configured to control the operation of such components. In an exemplary embodiment, the controller 52 may be configured to receive signals, information, measurements, and/or other data from the first and second sensors 32, 34 of the temperature probe 10, and to calculate and/or otherwise determine a core temperature of the patient based on the information received. The controller 52 may also be configured to execute one or more commands and/or control programs. For example, the controller 52 may be programmed to initiate one or more alarms in response to calculating a core temperature that is greater than or equal to a predetermined threshold temperature. In an exemplary embodiment, such a threshold temperature may be approximately 100° F. In addition, the controller 52 may be configured to initiate such an alarm during a substantially continuous temperature calculation operation if the calculated temperature increases and/or decreases at a rate that is greater than or equal to a predetermined threshold temperature change rate. The controller 52 may comprise a processor, memory, and/or other known controller components to facilitate the functionality described herein.

In an exemplary embodiment, the controller 52 may be disposed within, for example, the handle 20 of the temperature probe 10. In such an embodiment, the controller 52 may be formed substantially integral with the temperature probe 10. For example, the handle 20 may form one or more substantially watertight and/or substantially hermetically sealed compartments for storing the various components of the controller 52. Alternatively, as shown in FIG. 1, the controller 52 may be formed separately from the temperature probe 10. In such exemplary embodiments, the controller 52 may comprise a housing that is formed separate from the handle 20. To facilitate communication between the temperature probe 10 and the controller 52 in such embodiments, the controller 52 may be operably connected to the temperature probe 10 via one or more wires, cables, Bluetooth, WiFi, radio, and/or other known hard-wired and/or wireless communication protocols. The controller 52 and/or the temperature probe 10 may further include any number of ports, connectors, transponders, receivers, antennae, and/or other known components to facilitate such connectivity and/or communication. As shown in FIG. 1, in an exemplary embodiment in which the controller 52 is formed separate from the temperature probe 10, the controller 52 may comprise a display 54 and one or more operator interfaces 56. The display 54 and operator interfaces 56 of the controller 52 may be structurally and/or functionally similar to the display 54 and operator interfaces 22 of the handle 20 described herein.

The probe cover 30 may be substantially cylindrical, and may have similar dimensions to that of the shaft 18. For example, the probe cover 30 may be incrementally longer than the shaft 18 so as to fit over substantially the entire shaft 18. The probe cover 30 may define an orifice 46 at a proximal end 42 thereof. Similar to the shaft 18, the probe cover 30 may also define a substantially atraumatic tip 38 at a distal end 40 thereof. The probe cover 30 may be formed from any medically approved material known in the art. Such materials may include, for example, plastics, polymers, and/or any of the other materials discussed above with regard to the temperature probe 10. Using such materials may enable, for example, the probe cover 30 to be repeatedly used and/or sanitized. Alternatively, in additional exemplary embodiments, the probe cover 30 may be configured for one-time usage.

In additional exemplary embodiments, the probe cover 30 may include one or more additional structures to facilitate usage with, insertion on, and/or removal from the temperature probe 10. For example, while the orifice 46 may be shaped, sized, and/or otherwise configured to accept the shaft 18 and to mate with one or more retention components 27 of the temperature probe 10, in further exemplary embodiments, at least a portion of the proximal end 42 of the probe cover 30 may include additional notches, cutouts, tabs, ribs, rings, flanges, and/or other retention components (not shown) configured to assist in connecting the probe cover 30 to and/or disconnecting the probe cover 30 from the temperature probe 10. For example, such retention components of the probe cover 30 may mate with the retention components 27 of the temperature probe 10 to facilitate retention of the probe cover 30 on the shaft 18 and/or ejection of the probe cover 30 from the shaft 18.

In still further exemplary embodiments, one or more additional sensors 28 may be disposed on the temperature probe 10 at a location useful for detecting the presence of the probe cover 30. For example, such sensors 28 may be disposed proximate the base 24 of the shaft 18 and configured to detect the proximal end 42 of the probe cover 30 once the shaft 18 has been inserted into the probe cover 30. In still further exemplary embodiments, such sensors 28 may be disposed proximate the tip 16 and configured to detect the distal end 40 of the probe cover 30 once the shaft 18 has been inserted into the probe cover 30. In such exemplary embodiments, the one or more sensors 28 may comprise, for example, a proximity sensor and/or any other like sensing device, and sensing the first temperature indicative of a temperature of the probe cover 30 may be performed in response to detecting the presence of the probe cover 30 on the shaft 18.

An exemplary temperature measurement system 100 of the present disclosure may include any of the temperature probes 10, controllers 52, and probe covers 30 described herein, as well as the various components thereof. In addition, exemplary temperature measurement systems 100 of the present disclosure may further include a storage container 58 (FIGS. 3, 4, 6, and 7), and as mentioned above, one or more probe covers 30 may be disposed within the storage container 58. The storage container 58 may have any shape, size, and/or other configuration convenient for storing a plurality of probe covers 30 therein. For example, the storage container 58 may be substantially box shaped, and may have a substantially rectangular, substantially square, and/or substantially hexagonal cross-sectional shape.

At least a portion of the storage container 58 may define one or more openings 60. Such exemplary openings 60 may be shaped, sized, located, and/or otherwise configured to assist in the removal of one or more probe covers 30 from the storage container 58. For example, such an opening 60 may be shaped and/or sized to permit passage of a probe cover 30 for removal from the storage container 58. Such an opening 60 may also be shaped and/or sized to permit removal of only a single probe cover 30 from the storage container 58 at one time. In such an exemplary embodiment, the opening 60 may assist in retaining the remaining probe covers 30 within the storage container 58 while, at the same time, facilitating removal of a single probe cover 30 for use with the temperature probe 10.

Figure 3:
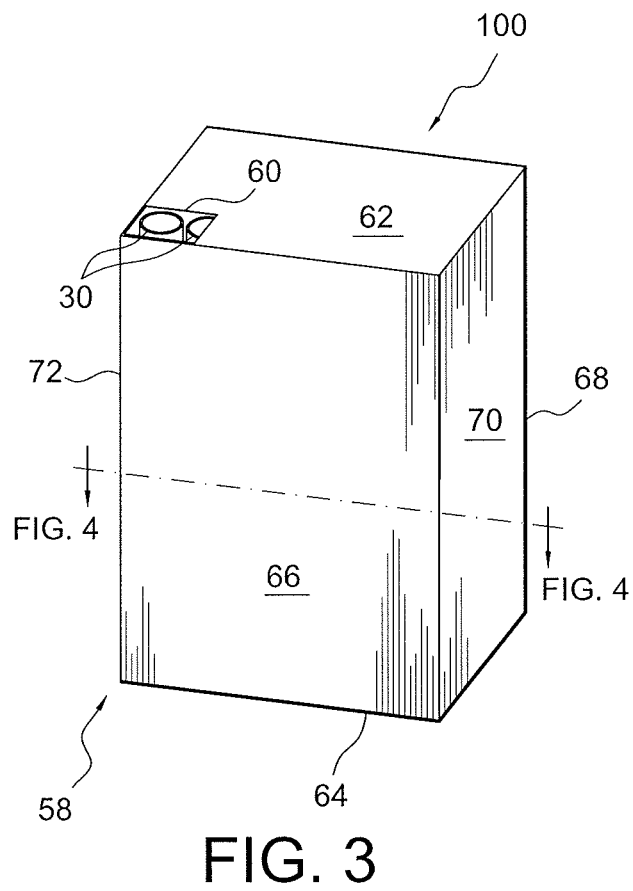
FIG. 3 illustrates a storage container of an exemplary temperature measurement system.
Figure 4:
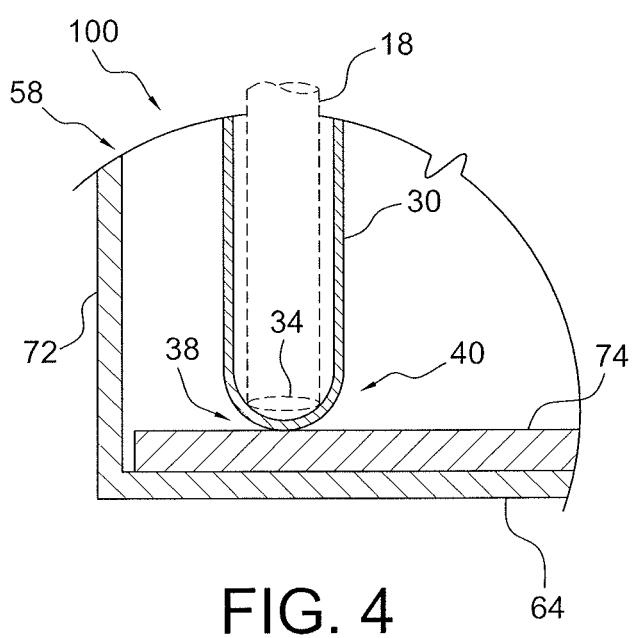
FIG. 4 is a cutaway view of a portion of the storage container shown in FIG. 3.

As shown in FIG. 3, the storage container 58 may include, for example, a front 66, a back 68, and at least two sides 70, 72. In additional exemplary embodiments, it is understood that the storage container 58 may include additional sides and/or other structures, depending upon, for example, the configuration of the probe covers 30 and/or storage requirements related to the probe covers 30. As shown in FIG. 3, an exemplary storage container 58 may also include a top 62 and a bottom wall 64 disposed opposite the top 62. The front 66, back 68, and at least two sides 70, 72 may be disposed orthogonal to the bottom wall 64. In an exemplary embodiment, the top 62 may define at least a portion of the opening 60. In additional exemplary embodiments, at least a portion of the top 62 may be removed to expose the opening 60, and in further exemplary embodiments, substantially the entire top 62 may be removed from the storage container 58. In such exemplary embodiments, substantially all of the probe covers 30 disposed within the storage container 58 may be exposed for removal.

As can be seen via the opening 60 illustrated in FIG. 3, two or more probe covers 30 may be positioned adjacently within the storage container 58. For example, two or more such probe covers 30 may be substantially aligned along respective lengths thereof within the storage container 58. In such exemplary embodiments, a plurality of probe covers 30 may be supported by, for example, the bottom wall 64 of the storage container 58, and may be arranged to stand within the storage container 58 on the respective distal ends 40 thereof.

As shown in FIG. 4, the conductor 74 described above may be disposed on the bottom wall 64 of the storage container 58, and the distal end 40 of each respective probe cover 30 disposed within the storage container 58 may be in contact with the conductor 74. In exemplary embodiments, the conductor 74 may extend along the bottom wall 64 from the front 66 to the back 68 of the storage container 58. The conductor 74 may also extend from the first side 70 to the second side 72 such that the conductor 74 covers substantially the entire bottom wall 64. Although FIG. 4 illustrates the conductor 74 being disposed on an inner surface of the bottom wall 64, in additional exemplary embodiments, the conductor 74 may be disposed on an outer surface of the bottom wall 64. As discussed above, in still further exemplary embodiments, the conductor 74 may be formed integrally with the bottom wall 64.

As shown in at least FIG. 4, when the shaft 18 is disposed within the probe cover 30 such that the capacitance sensor 34 is disposed adjacent to and/or in contact with the tip 38 of the probe cover 30, the capacitance sensor 34 may be configured to measure a change in capacitance resulting from the capacitance sensor 34 being separated from the conductor 74 by the probe cover 30. For instance, the capacitance measured by the capacitance sensor 34 when disposed as shown in FIG. 4 may be different than a capacitance measured if the capacitance sensor 34 of FIG. 4 was disposed in direct contact with the conductor 74 on the bottom wall 64. Although not described in greater detail herein, in further exemplary embodiments the capacitance sensor 34 may be configured to measure a change in capacitance caused by relative movement between the capacitance sensor 34 and the conductor 74.

The temperature probes 10, probe covers 30, and storage containers 58 described herein may be utilized by physicians, nurses, and/or other healthcare professionals in a variety of different environments. For example, the devices and/or the temperature measurement systems 100 described herein may be employed in any of a number of examination facilities to determine one or more temperatures associated with a patient, such as, for example, a core temperature of the patient. Such a temperature determination may be utilized by the healthcare professional to assist in treating the patient, and may have a variety of uses that are well known in the medical field.

For example, the user may insert at least a portion of the temperature probe 10, such as the shaft 18, into the probe cover 30 via the orifice 46. In an exemplary embodiment, the probe cover 30 may be disposed within a storage container 58 while the shaft 18 of the temperature probe 10 is inserted into the probe cover 30. In such an exemplary embodiment, the probe cover 30 may be accessed through the opening 60 of the storage container 58 for insertion of the shaft 18. In such an exemplary embodiment, the temperature probe 10 may be moved in the direction of arrow 50 (FIG. 1) relative to the probe cover 30 for insertion. Alternatively, in exemplary embodiments in which the probe cover 30 has been removed from the storage container 58 before connection with the temperature probe 10, the probe cover 30 may be moved in the direction of arrow 48 (FIG. 1) relative to the temperature probe 10 to facilitate a connection with the temperature probe 10.

As one or more of the retention components 27 of the temperature probe 10 come into contact with the probe cover 30, such retention components 27 may hook, clip, and/or otherwise mate with the proximal end 42 of the probe cover 30 to assist in retaining the probe cover 30 on the shaft 18. In exemplary embodiments in which the proximal end 42 of the probe cover 30 defines one or more of the notches, cutouts, and/or other retention components described above, the retention components of the probe cover 30 may communicate with the retention components 27 of the temperature probe 10 to assist in retaining the probe cover 30 thereon.

For example, the user may dispose the shaft 18 within the probe cover 30 such that a capacitance sensor 34 disposed proximate the distal end 15 of the shaft 18 is positioned proximate the distal end 40 of the probe cover 30. The shaft 18, along with the probe cover 30, may then be disposed within a body cavity of the patient, and the capacitance sensor 34 may be activated to measure and/or otherwise determine a first capacitance associated with the body cavity. In such an exemplary embodiment, the body cavity may constitute a conductor 74, and a virtual capacitor may be formed by the capacitance sensor 34 and the body cavity.

Figure 10:
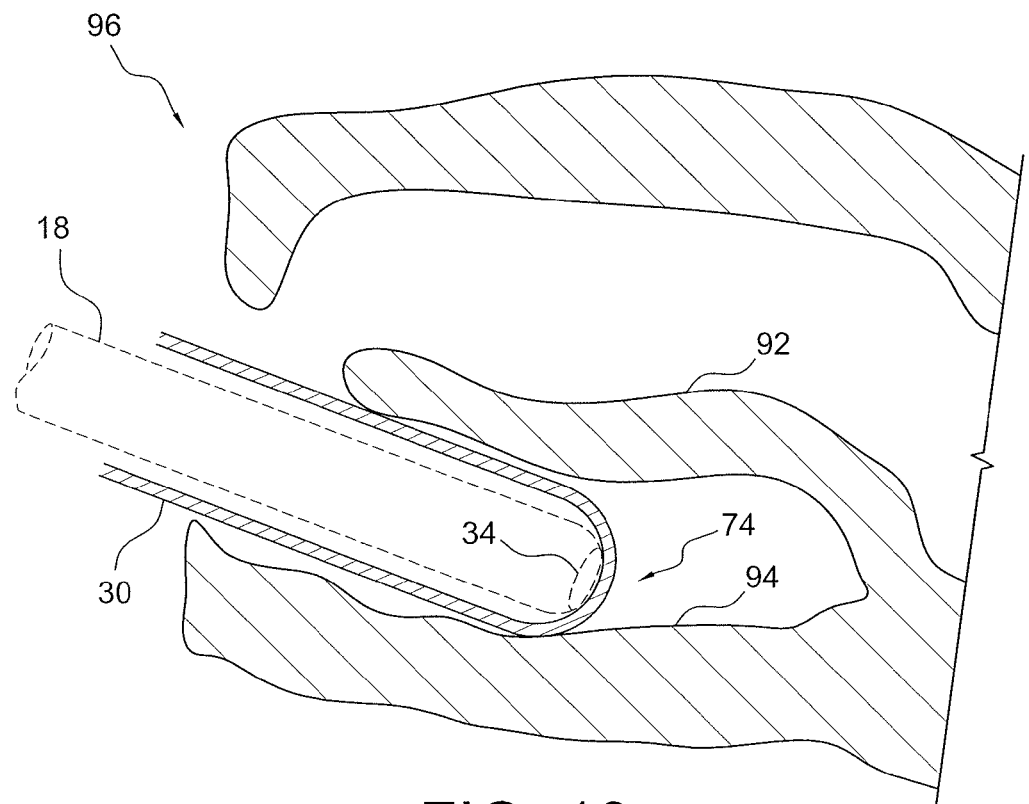
FIG. 10 illustrates a partial view of a mouth of a patient according to an exemplary embodiment of the present disclosure.

For example, FIG. 2 illustrates an exemplary capacitance plot corresponding to an embodiment of the temperature measurement system 100 in which the capacitance sensor 34 is disposed proximate the distal end 15 of the shaft 18, and the conductor 74 comprises a body cavity of the patient. An exemplary embodiment in which the conductor 74 comprises a body cavity of the patient, such as, for example, a mouth 96 of the patient is illustrated in FIG. 10. In the exemplary embodiment shown in FIG. 10, the probe cover 30 may be disposed in contact with, for example, the tongue 92, and/or an internal mouth surface 94 of the patient. In such exemplary embodiments, the tongue 92 and/or the mouth surface 94 may comprise the conductor 74.

As shown in FIG. 2, one or more known and/or reference capacitance values may be stored in the memory of the controller 52. Such values may correspond to, for example, a capacitance sensed without a probe cover 30 being disposed on the shaft 18 and the capacitance sensor 34 being in direct contact with the conductor 74 (e.g., 700 counts), a capacitance sensed with a reference probe cover 30 having a thickness of 0.010 inches disposed on the shaft 18 (e.g., 400 counts), and a capacitance sensed with a reference probe cover 30 having a thickness of 0.015 inches disposed on the shaft 18 (e.g., 380 counts). It is understood that the reference capacitance values corresponding to the 0.010-inch and 0.015-inch probe covers 30 may vary depending on, for example, the type of conductor 74, the location of the capacitance sensor 34 relative to the probe cover 30, the location of the capacitance sensor 34 relative to the conductor 74, and/or other factors related to the particular configuration of the temperature measurement system 100.

In the exemplary core temperature determination described above with respect to FIG. 2, if the first capacitance determined by the capacitance sensor 34 corresponds to a capacitance value of 387 counts, the controller 52 may determine a difference between the first capacitance and one of the stored reference capacitance values to determine an unknown thickness of the probe cover 30. For example, the controller 52 may extrapolate between the two reference capacitance values discussed above to determine the thickness of the probe cover 30 used during measurement of the first capacitance. In alternative exemplary embodiments, the controller 52 may use any other known mathematical and/or functional relationships to determine the thickness of the probe cover 30, and in further exemplary embodiments, the controller 52 may use one or more stored look-up tables to determine such a thickness. This determined thickness may be used by the controller 52 as an input to a core temperature determination algorithm. For example, the controller 52 may determine the core temperature of the patient based on the determined thickness of the probe cover 30 being used as well as a temperature of the body cavity as measured by the temperature sensor 32.

While the capacitance plot shown in FIG. 2 is illustrative of an exemplary embodiment, such as the embodiment shown in FIG. 10, in which the body cavity of the patient comprises the conductor 74, in further exemplary core temperature determination methods, a conductor 74 disposed on the bottom wall 64 of the storage container 58 or on the base 86 of a receptacle 84 may be used to measure a change in capacitance. For example, the capacitance plot shown in FIG. 5 is illustrative of the exemplary embodiment of FIG. 4 in which the capacitance sensor 34 is disposed at the tip 16 of the shaft 18, the tip 16 is disposed adjacent to the tip 38 of the probe cover 30, and the distal end 40 of the probe cover 30 is in contact with a conductor 74 disposed on the bottom wall 64 of the storage container 58. In such an exemplary embodiment, the capacitance sensor 34 may be separated from the conductor 74 by the relatively thin probe cover 30, and the capacitance sensor 34 may measure a change in capacitance resulting from the capacitance sensor 34 being separated from the conductor 74 by the distal end 40 of the probe cover 30. As shown in FIG. 5, in such an exemplary embodiment, an exemplary reference capacitance value corresponding to a 0.010-inch probe cover 30 may be 690 counts and an exemplary reference capacitance value corresponding to a 0.015-inch probe cover 30 may be 680 counts. Such reference capacitance values may be higher than, for example, the values discussed above with respect to FIG. 2 due to the type of conductor 74 shown in FIG. 4, and the proximity of the capacitance sensor 34 shown in FIG. 4 to the conductor 74. In the exemplary embodiment of FIGS. 4 and 5, if the first capacitance determined by the capacitance sensor 34 corresponds to a capacitance value of 687 counts, the controller 52 may determine a difference between the first capacitance and one of the stored reference capacitance values to determine an unknown thickness of the probe cover 30. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

The capacitance plot shown in FIG. 8 is illustrative of the exemplary embodiment of FIG. 7 in which the capacitance sensor 34 is disposed at the tip 16 of the shaft 18, the tip 16 is disposed adjacent to the tip 38 of the probe cover 30, and the distal end 40 of the probe cover 30 is in contact with the bottom wall 64 of the storage container 58. The bottom wall 64 is disposed on the base 86 of the receptacle 84, and the conductor is disposed on the inner surface 88 of the base 86. In this exemplary embodiment, the capacitance sensor 34 is separated from the conductor 74 by the probe cover 30 and the bottom wall 64, and the capacitance sensor 34 may measure a change in capacitance resulting from the capacitance sensor 34 being separated from the conductor 74 by the distal end 40 of the probe cover 30 and the bottom wall 64. As shown in FIG. 8, in such an exemplary embodiment, an exemplary reference capacitance value corresponding to a 0.010-inch probe cover 30 may be 650 counts and an exemplary reference capacitance value corresponding to a 0.015-inch probe cover 30 may be 640 counts. While such reference capacitance values may be higher than, for example, the values discussed above with respect to FIG. 2, such values may be slightly lower than the values discussed above with respect to FIG. 5 due to the proximity of the capacitance sensor 34 shown in FIG. 7 to the conductor 74. In the exemplary embodiment of FIGS. 7 and 8, if the first capacitance determined by the capacitance sensor 34 corresponds to a capacitance value of 647 counts, the controller 52 may determine a difference between the first capacitance and one of the stored reference capacitance values to determine an unknown thickness of the probe cover 30. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

In additional exemplary core temperature determination methods, a conductor 74 disposed at a proximal end of the shaft 18 may be used to measure a change in capacitance. For example, the capacitance plot shown in FIG. 5 may also be illustrative of the exemplary embodiment of FIG. 9 in which the capacitance sensor 34 is disposed proximate the proximal end 13 of the shaft 18, such as on the base 24 of the shaft 18. Additionally, the conductor 74 may be a metallic ring encircling a portion of the proximal end 13. The conductor 74 may overlay a portion of the capacitance sensor 34, and the probe cover 30 may be disposed on the shaft 18 between the capacitance sensor 34 and the conductor. In such an exemplary embodiment, the capacitance sensor 34 may be separated from the conductor 74 by the relatively thin probe cover 30 and an additional gap or clearance provided between the conductor 74 and the probe cover 30 for connection and/or disconnection of the probe cover 30. The capacitance sensor 34 may measure a change in capacitance resulting from the probe cover 30 being disposed between the capacitance sensor 34 and the ring-shaped conductor 74. This process may be similar to the methods described above with regard to FIG. 2. Additionally, as described above with respect to FIG. 2, the controller 52 may determine the core temperature of the patient based on the determined thickness of the probe cover 30 as well as a temperature of the body cavity as measured by the temperature sensor 32.

In the exemplary core temperature determination methods described herein, the sensor 32 may be activated to sense a temperature of the body cavity while the shaft 18 is disposed within the body cavity. For example, in an embodiment in which the first sensor 32 comprises a thermocouple and/or a thermistor, the first sensor 32 may be utilized to measure the temperature of the body cavity. Further, in any of the exemplary embodiments described herein, sensing the body cavity temperature may be sensed by activating one or more infrared temperature sensors of the temperature probe 10, such as one or more of the thermopiles described above.

Signals indicative of the measured change in capacitance and the measured body cavity temperature may be sent to the controller 52 by the first and second sensors 32, 34, and the controller 52 may assist in determining the core temperature based on the capacitance and the measured temperature. For example, determining the thickness of the probe cover 30 based on the sensed capacitance change may assist in accurately determining such a core temperature. In exemplary embodiments, such capacitance and a corresponding thickness of the probe cover 30 may be utilized in the core temperature calculation to reduce error. Such error is commonly caused by using an inaccurate estimate of probe cover thickness and a corresponding inaccurate effect of such thickness on the measured body cavity temperature. It is understood that even small discrepancies between the actual and estimated probe cover thickness may have a dramatic effect on the resulting core temperature determined by the controller 52. The exemplary embodiments of the present disclosure, on the other hand, substantially eliminate such error from the core temperature determination.

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

What is claimed is:
1. A temperature probe, comprising:
a handle;
a shaft extending from the handle, the shaft having a distal end, a proximal end, and a tip at the distal end;

a capacitance sensor disposed on one of the handle and the shaft, the capacitance sensor configured to measure a change in capacitance when positioned proximate a conductor;

a temperature sensor disposed on the shaft, the temperature sensor configured to measure a body cavity temperature of a patient; and a controller in communication with the temperature sensor and the capacitance sensor, wherein the controller is configured to determine a patient temperature based on a) the body cavity temperature, and b) a difference between a first capacitance measured by the capacitance sensor and a known capacitance stored in a memory associated with the controller.

2. The probe of claim 1, wherein the capacitance sensor is disposed proximate the distal end of the shaft, and the conductor comprises a body cavity of the patient.

3. The probe of claim 1, wherein the capacitance sensor is disposed at the tip of the shaft, and the conductor comprises a metallic sheet separated from the tip by a probe cover disposed on the shaft.

4. The probe of claim 3, wherein the probe cover is disposed within a storage container and the conductor is disposed on a bottom wall of the storage container.

5. The probe of claim 3, wherein the probe cover is disposed within a storage container and the storage container is disposed within a receptacle, the conductor being disposed on a base of the receptacle.

6. The probe of claim 1, wherein the capacitance sensor is disposed proximate the proximal end and the conductor comprises a metallic ring encircling a portion of the proximal end.

7. The probe of claim 6, wherein the metallic ring is connected to the probe and is spaced from an outer surface of the shaft, a probe cover being disposed on the shaft between the metallic ring and a portion of the capacitance sensor.

8. The probe of claim 1, wherein the controller is configured to determine the patient temperature based on the measured body cavity temperature and a signal received from the capacitance sensor indicative of a thickness of a probe cover.

9. The probe of claim 8, wherein the signal received from the capacitance sensor is indicative of the change in capacitance, and wherein the change in capacitance is based on a distance between the capacitance sensor and the conductor.

10. The probe of claim 8, wherein the signal is indicative of a capacitance measured by the capacitance sensor while the probe cover is disposed on the shaft between the capacitance sensor and the conductor.

11. The probe of claim 1, wherein the capacitance sensor comprises a single conductive layer configured to generate an electric field extending therefrom, the conductor comprises a body cavity of the patient, and the first capacitance comprises a change in capacitance resulting from the body cavity being disposed within the electric field extending from the conductive layer.

12. The probe of claim 1, wherein the patient temperature is determined from a group consisting of a core temperature of the patient and an internal temperature of the patient.

13. The probe of claim 1, wherein the controller uses a value indicative of the difference as an input in a patient temperature calculation.

14. The probe of claim 13, wherein using a first value, indicative of a first difference, in a first patient temperature calculation yields a first patient temperature, and wherein using a second value, indicative of a second difference, in a second patient temperature yields a second patient temperature different from the first patient temperature.

15. A method of determining a core temperature of a patient, comprising:

determining a first capacitance with a capacitance sensor of a temperature probe;

determining a difference between the first capacitance and a known capacitance stored in a memory associated with the temperature probe;

inserting a portion of the temperature probe into a body cavity of the patient;

measuring a body cavity temperature of the patient with the temperature probe; and calculating the core temperature of the patient based on the difference and the body cavity temperature.

16. The method of claim 15, wherein measuring the body cavity temperature of the patient comprises activating one of a thermistor and an infrared temperature sensor disposed at a proximal end of the temperature probe.

17. The method of claim 15, wherein determining the first capacitance comprises inserting a shaft of the temperature probe into a probe cover disposed within a storage container, the storage container having a bottom wall and a conductor disposed on the bottom wall in contact with a distal end of the probe cover, and measuring a change in capacitance resulting from the capacitance sensor being separated from the conductor by the distal end of the probe cover.

18. The method of claim 15, wherein determining the first capacitance comprises inserting a shaft of the temperature probe into a probe cover disposed within a storage container, the storage container being disposed within a receptacle having a base and a conductor disposed on the base, and measuring a change in capacitance resulting from the capacitance sensor being separated from the conductor by a distal end of the probe cover and a bottom wall of the storage container.

19. The method of claim 15, wherein determining the first capacitance comprises inserting a shaft of the temperature probe into a probe cover such that the probe cover is disposed between the capacitance sensor and a metallic ring encircling a portion of the proximal end of the shaft, and measuring a change in capacitance resulting from the probe cover being disposed between the capacitance sensor and the metallic ring.

20. The method of claim 15, wherein determining the first capacitance comprises determining a change in capacitance based on a distance between the capacitance sensor and a conductor.

* * * * *